(12) United States Patent  
Wang et al.

(10) Patent No.: US 7,545,493 B2
(45) Date of Patent: Jun. 9, 2009

(54) RAMAN SPECTROSCOPIC APPARATUS UTILIZING INTERNAL GRATING STABILIZED SEMICONDUCTOR LASER WITH HIGH SPECTRAL BRIGHTNESS

(75) Inventors: Sean Xiaolu Wang, Wilmington, DE (US); Qun Li, Newark, DE (US)

(73) Assignee: BWT Property, Inc., Newark, DE (US)

( * ) Notice: Subject to any disclaimer, the term of this patent is extended or adjusted under 35 U.S.C. 154(b) by 50 days.

(21) Appl. No.: 11/608,237

(22) Filed: Dec. 7, 2006

(65) Prior Publication Data

US 2007/0146699 A1 Jun. 28, 2007

Related U.S. Application Data

(60) Provisional application No. 60/597,911, filed on Dec. 23, 2005.

(51) Int. Cl.
G01J 3/44 (2006.01)
(52) U.S. Cl. .................................................. 356/301
(58) Field of Classification Search ................ 356/301
See application file for complete search history.

(56) References Cited

U.S. PATENT DOCUMENTS

| | | | |
|---|---|---|---|
| 3,866,032 A | 2/1975 | Veres | |
| 4,034,480 A | 7/1977 | Mehrtens | |
| 4,064,424 A | 12/1977 | Hergenrother | |
| 4,183,078 A | 1/1980 | Kidd | |
| 4,430,695 A | 2/1984 | Payne et al. | |
| 4,532,512 A | 7/1985 | Tanner | |
| 5,139,334 A | 8/1992 | Clarke et al. | |
| 5,224,773 A | 7/1993 | Arimura | |
| 5,287,104 A | 2/1994 | Shemwell | |
| 5,377,683 A | 1/1995 | Barken | |
| 5,608,290 A | 3/1997 | Hutchisson | |
| 5,655,308 A | 8/1997 | McDermott | |
| 5,804,829 A | 9/1998 | Palmer | |
| 5,856,869 A * | 1/1999 | Cooper et al. ............... 356/301 |
| 5,967,984 A | 10/1999 | Chu et al. | |
| 5,982,484 A | 11/1999 | Clarke et al. | |
| 6,007,219 A | 12/1999 | O'Meara | |
| 6,030,099 A | 2/2000 | McDermott | |
| 6,048,083 A | 4/2000 | McDermott | |
| 6,086,220 A | 7/2000 | Lash et al. | |
| 6,100,975 A | 8/2000 | Smith et al. | |
| 6,135,994 A | 10/2000 | Chernoff | |
| 6,168,294 B1 | 1/2001 | Erni et al. | |
| 6,224,216 B1 | 5/2001 | Parker et al. | |
| 6,354,714 B1 | 3/2002 | Rhodes | |
| 6,446,467 B1 | 9/2002 | Lieberman et al. | |
| 6,464,373 B1 | 10/2002 | Petrick | |
| 6,489,733 B1 | 12/2002 | Schmidt et al. | |
| 6,543,911 B1 | 4/2003 | Rizkin et al. | |
| 6,563,854 B2 | 5/2003 | Tedesco et al. | |
| 6,688,755 B2 | 2/2004 | O'Meara | |

(Continued)

*Primary Examiner*—Kara E Geisel
(74) *Attorney, Agent, or Firm*—Frank F. Tian

(57) ABSTRACT

A Raman spectroscopic apparatus utilizing a broad stripe semiconductor laser as the excitation light source is provided. The output spectrum of the semiconductor laser is narrowed and stabilized by an internal grating to provide high spectral brightness. A high throughput optical system is also disclosed for Raman scattering signal excitation and extraction, which takes full advantage of the high spectral brightness of the laser source.

9 Claims, 7 Drawing Sheets

U.S. PATENT DOCUMENTS

| | | | |
|---|---|---|---|
| 6,734,963 B2 * | 5/2004 | Gamble et al. | 356/301 |
| 6,753,762 B1 | 6/2004 | Jorba Gonzalez | |
| 6,902,291 B2 | 6/2005 | Rizkin et al. | |
| 6,905,228 B1 | 6/2005 | Takeyasu et al. | |
| 6,932,496 B2 | 8/2005 | Rizkin et al. | |
| 6,947,571 B1 | 9/2005 | Rhoads et al. | |
| 7,021,801 B2 | 4/2006 | Mohacsi | |
| 2003/0136837 A1 | 7/2003 | Amon | |
| 2003/0187742 A1 | 10/2003 | Yamagishi | |
| 2004/0095777 A1 | 5/2004 | Trenchard et al. | |
| 2005/0105084 A1 * | 5/2005 | Wang et al. | 356/301 |
| 2005/0110649 A1 | 5/2005 | Fredericks et al. | |
| 2005/0111723 A1 | 5/2005 | Hannigan et al. | |
| 2005/0163186 A1 * | 7/2005 | Petersen | 372/93 |
| 2006/0082760 A1 | 4/2006 | Lin | |
| 2006/0250801 A1 | 11/2006 | Trenchard et al. | |

* cited by examiner

600 providing a broad stripe diode laser with an internal grating for producing a laser beam with high spectral brightnes
602

providing an optical system for delivering said laser beam to a physical material to excite a scattered optical signal, and for extracting a Raman scattering signal from the scattered optical signal, said optical system utilizes the high spectral brightness of the laser for efficient Raman scattering excitation and extraction
604

providing a spectrograph for measuring the relative intensity of different wavelength components of the Raman scattering signal to obtain a Raman spectrum
606

FIG. 6

700 providing a plurality of broad stripe diode lasers with internal gratings
702 obtaining a plurality of Raman/fluorescence spectra from the physical material by using the plurality of broad stripe diode lasers as the excitation light source
704 mathematically manipulating the plurality of Raman/fluorescence spectra to extract a Raman spectrum from the plurality of Raman/fluorescence spectra
706

FIG. 7

RAMAN SPECTROSCOPIC APPARATUS UTILIZING INTERNAL GRATING STABILIZED SEMICONDUCTOR LASER WITH HIGH SPECTRAL BRIGHTNESS

REFERENCE TO RELATED APPLICATIONS

This application claims an invention which was disclosed in Provisional Patent Application No. 60/597,911, filed Dec. 23, 2005, entitled "Raman Spectroscopy Apparatus Utilizing Internal Grating Stabilized Semiconductor Laser with High Spectral Brightness". The benefit under 35 USC §119(e) of the above mentioned United States Provisional applications is hereby claimed, and the aforementioned application is hereby incorporated herein by reference.

FIELD OF THE INVENTION

This invention generally relates to a Raman spectroscopic apparatus, and more specifically to a Raman spectroscopic apparatus utilizing an internal grating stabilized semiconductor laser with high spectral brightness as the excitation light source.

BACKGROUND

The deployment of Raman spectroscopy has been hindered by the lack of a low cost, rugged and stable semiconductor laser source that can provide high spectral brightness, where the spectral brightness is defined as laser power divided by its spectral linewidth. A broad stripe or broad area diode laser (e.g. with a stripe width typically in the range of 20-500 μm) can provide a high output power of >1 W, while its spectral linewidth is on the order of several nanometers or more due to the existence of a large number of lasing modes in the Fabry-Perot (F-P) laser cavity. This broad linewidth limits the broad stripe laser only to those low resolution Raman spectroscopy applications as disclosed by Clarke et al. in U.S. Pat. Nos. 5,139,334 and 5,982,484. On the other hand, the output power of a single mode diode laser (with a stripe width of a few micrometers) is typically limited to a few hundred milliwatts. This power level is inadequate for Raman spectroscopic analysis of some materials with not so strong Raman scattering. An example of the application of a single mode DBR laser for Raman spectroscopy can be found in U.S. Pat. No. 5,856,869 disclosed by Cooper et al.

Recently, it has been demonstrated that an external cavity laser (ECL) structure can be used to narrow down the linewidth of a broad stripe laser as disclosed by Smith et al. in U.S. Pat. No. 6,100,975 and by Tedesco et al. in U.S. Pat. No. 6,563,854. In these references, the lasing wavelength of the diode laser is locked by an external grating that is positioned a distance away from the semiconductor laser chip to form an external cavity. However, the ECL structure is relatively complicated and the long cavity length may result in mechanical and thermal instability.

Therefore, there is a need for an improved Raman spectroscopic apparatus that utilizes a more rugged and stable semiconductor laser source with high spectral brightness to provide better sensitivity and spectral resolution.

SUMMARY OF THE INVENTION

It is thus the overall goal of the present invention to solve all the above-mentioned problems and provide a Raman spectroscopic apparatus which utilizes an internal grating stabilized broad stripe diode laser as the excitation light source. In the present invention, the internal grating is monolithically integrated with the diode laser in the same semiconductor structure. The laser exhibits a high output power and a narrow spectral linewidth, i.e. a high spectral brightness as well as a good spectral stability.

It is another goal of the present invention to optimize the optical system for Raman scattering signal excitation and extraction in order to take full advantage of the high spectral brightness of the laser source.

It is yet another goal of the present invention to provide a multi-wavelength laser source and a shifted wavelength excitation technique for fluorescence suppression in Raman spectroscopy.

A Raman spectroscopic apparatus for measuring the Raman spectrum of a physical material is provided. The apparatus comprises: an internal grating stabilized, broad stripe diode laser for producing a laser beam; an optical system for delivering said laser beam to a physical material to excite a scattered optical signal, and for extracting a Raman scattering signal from the scattered optical signal, said optical system utilizes the high spectral brightness of the laser for efficient Raman scattering excitation and extraction; and a spectrograph to collect said Raman scattering signal and disperse the Raman scattering signal into a plurality of wavelength components for spectral measurement.

A method for measuring the Raman spectrum of a physical material is provided. The method comprises the steps of: providing an internal grating stabilized, broad stripe diode laser for producing a laser beam; providing an optical system for delivering said laser beam to a physical material to excite a scattered optical signal, and for extracting a Raman scattering signal from the scattered optical signal, said optical system utilizes the high spectral brightness of the laser for efficient Raman scattering excitation and extraction; and providing a spectrograph to collect said Raman scattering signal and disperse the Raman scattering signal into a plurality of wavelength components for spectral measurement.

A method is provided for measuring the Raman spectrum of a physical material that exhibits fluorescence. The method comprises the steps of: providing a plurality of broad stripe diode lasers with internal gratings. The lasers have slightly shifted laser wavelengths as determined by slightly shifted Bragg wavelengths of the internal gratings. The method further comprises the steps of obtaining a plurality of Raman/fluorescence spectra from the physical material by using the plurality of broad stripe diode lasers as the excitation light source; and mathematically manipulating the plurality of Raman/fluorescence spectra to extract a Raman spectrum from the plurality of Raman/fluorescence spectra.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 6 is a first flowchart of the present invention.

FIG. 7 is a second flowchart of the present invention.

Figure 1:
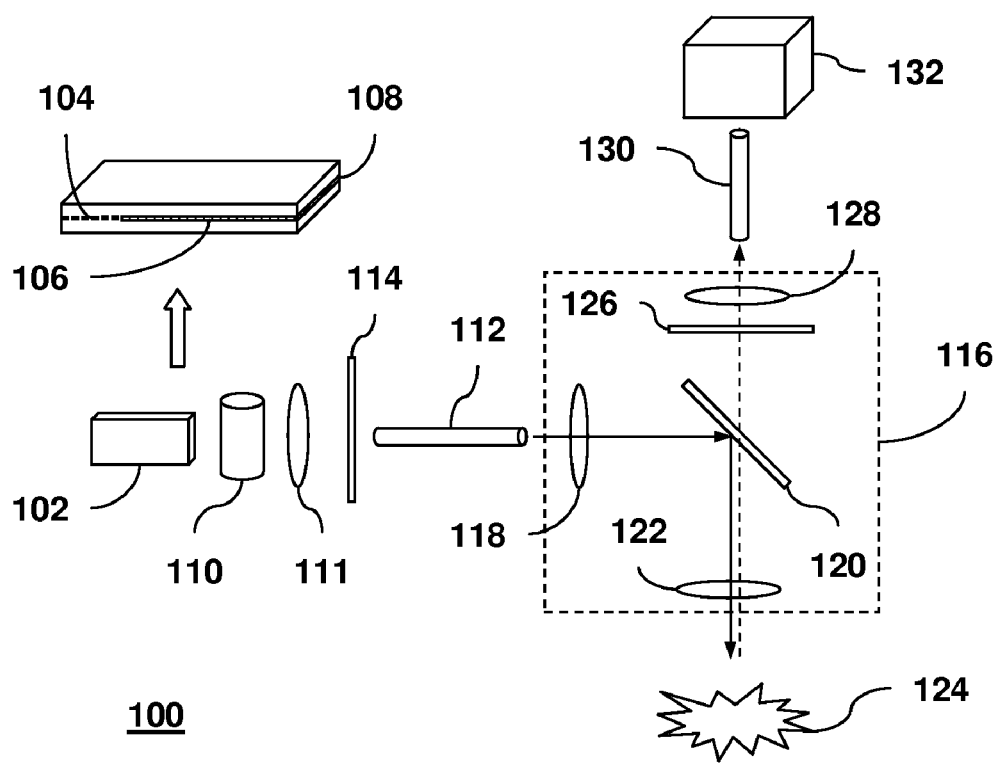
FIG. 1 illustrates a block diagram of the disclosed Raman spectroscopic apparatus utilizing an internal grating stabilized broad stripe diode laser as its excitation light source.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a Raman spectroscopic apparatus utilizing an internal grating stabilized semiconductor laser with high spectral brightness as the excitation light source. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

A preferred embodiment of the present invention is shown in FIG. 1. In FIG. 1, the Raman spectroscopic apparatus 100 comprises a broad stripe diode laser 102 as its excitation light source. The output spectrum of the laser 102 is narrowed and stabilized by an internal grating 104 acting as a distributed Bragg reflector (DBR). The active region 106 of the laser features a stripe width of around 100 μm and a cavity length of around 1500 μm, where the laser cavity is defined by the internal grating 104 and a cleaved surface 108 at output end of the laser. The internal grating 104 provides a narrowband reflection at its Bragg wavelength that is determined by the grating period. Thus the lasing wavelength is locked to the Bragg wavelength and the spectral linewidth of the laser is reduced by an order of magnitude in comparison to broad stripe lasers with a Fabry-Perot (F-P) cavity. The maximum output power of the internal grating stabilized broad stripe diode laser 102 can easily scale up to several watts. The internal grating technology eliminates the need for any external optical elements as in an ECL laser and increases the overall robustness of the laser. In the present embodiment, the laser 102 has a central emission wavelength at around 988 nm.

Figure 2:
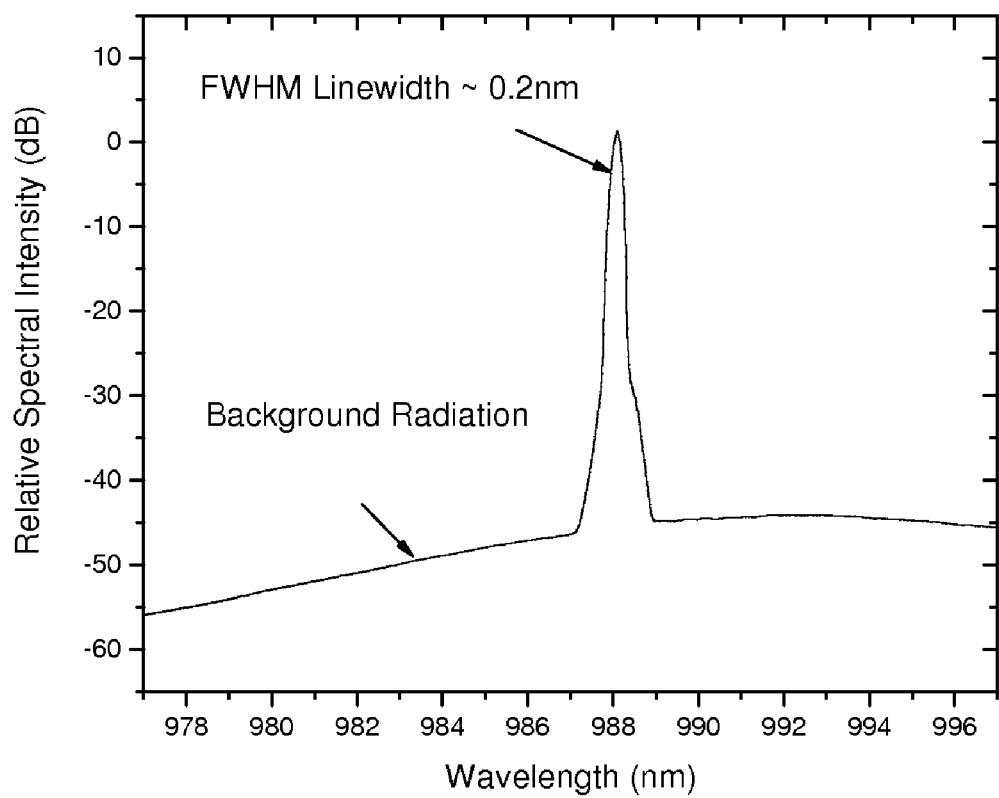
FIG. 2 shows the measured laser output spectrum by an optical spectrum analyzer.

FIG. 2 shows the emission spectrum of the laser measured with an ANDO AQ6317B optical spectrum analyzer at a wavelength resolution of 0.01 nm. The laser exhibits a FWHM (full-width at half-maximum) linewidth of about 0.2 nm and a maximum output power of >2.5 W. The side mode suppression ratio of the laser (defined by the intensity ratio between the main laser line and the background radiation) is >45 dB. The temperature sensitivity of the laser wavelength is about 0.08 nm/° C., which is three times lower than that of a broad stripe F-P laser. The internal grating also helps to reduce the divergence angle of the laser beam, thus increases the beam's spatial brightness. Here the spatial brightness is defined as the intensity of the laser beam divided by its divergence angle. A more detailed discussion about the internal grating stabilized laser can be found in R. M. Lammert, S. W. Oh, M. L. Osowski, C. Panja, P. T. Rudy, T. Stakelon, and J. E. Ungar, "Advances in high-brightness high-power semiconductor lasers", Proceedings of SPIE, Vol. 6216, 62160B, May 12, 2006, which is hereby incorporated herein by reference.

The Raman spectroscopic apparatus 100 further comprises an optical system for laser light delivery and Raman scattering signal collection, which is optimized to take full advantage of the high spectral brightness of the laser source. The light from the laser 102 is first collimated by a cylindrical lens 110 and then focused by another optical lens 111, e.g. an aspherical lens to be coupled into a multimode optical fiber 112 with a numerical aperture (NA) of about 0.22 and a core diameter of about 50 μm. The numerical aperture and core diameter of the fiber 112 is selected to match with the divergence angle and spot size of the collimated laser beam, respectively to maintain the beam's spatial brightness. A shortpass optical filter 114 with a cutoff wavelength of about 1000 nm is inserted between the optical lens 111 and the optical fiber 112 to further suppress the background radiation of the laser at longer wavelengths. The laser light is delivered by the optical fiber 112 into an optical probe 116 for excitation and collection of the Raman scattering signal. The optical probe 116 comprises a first optical lens 118 with an effective focal length of around 8 mm to collect and collimate the laser beam emitted from the optical fiber 112. The collimated laser beam is then reflected by a dichroic filter 120 with a cutoff wavelength at around 1000 nm to a second optical lens 122. The optical lens 122 has a small focal length of about 3.1 mm to focus the laser beam onto a sample 124 to excite Raman scattering from the sample 124. The high spatial brightness of the internal grating stabilized laser 102 makes it possible to focus the laser beam into a small spot for efficient Raman scattering excitation. The optical lens 122 also features a large numerical aperture of about 0.68 for efficient collection of the Raman scattering signal. The collected Raman scattering signal is collimated by the optical lens 122 and passes through the dichroic filter 120 for filtering out the Rayleigh scattering and the reflected laser light from the sample 124. A longpass optical filter 126 following the dichroic filter 120 is used to further remove the Rayleigh scattering from the Raman scattering signal. The filter 126 has a cutoff wavelength at around 1064 nm and provides a rejection ratio of >6 OD (60 dB) for optical wavelengths of <1064 nm and a transmission of >90% for optical wavelengths of >1064 nm. The filtered Raman scattering signal is focused by a third optical lens 128 with a focal length of around 25 mm into another multimode optical fiber 130. The fiber 130 has a core diameter of about 200 μm and an NA of about 0.22 for collecting the filtered Raman scattering signal and delivering it into an InGaAs array spectrograph 132 for spectral analysis. The wavelength covering range of the spectrograph 132 is from about 900 nm to about 1700 nm with a wavelength resolution of about 1.6 nm.

Figure 3:
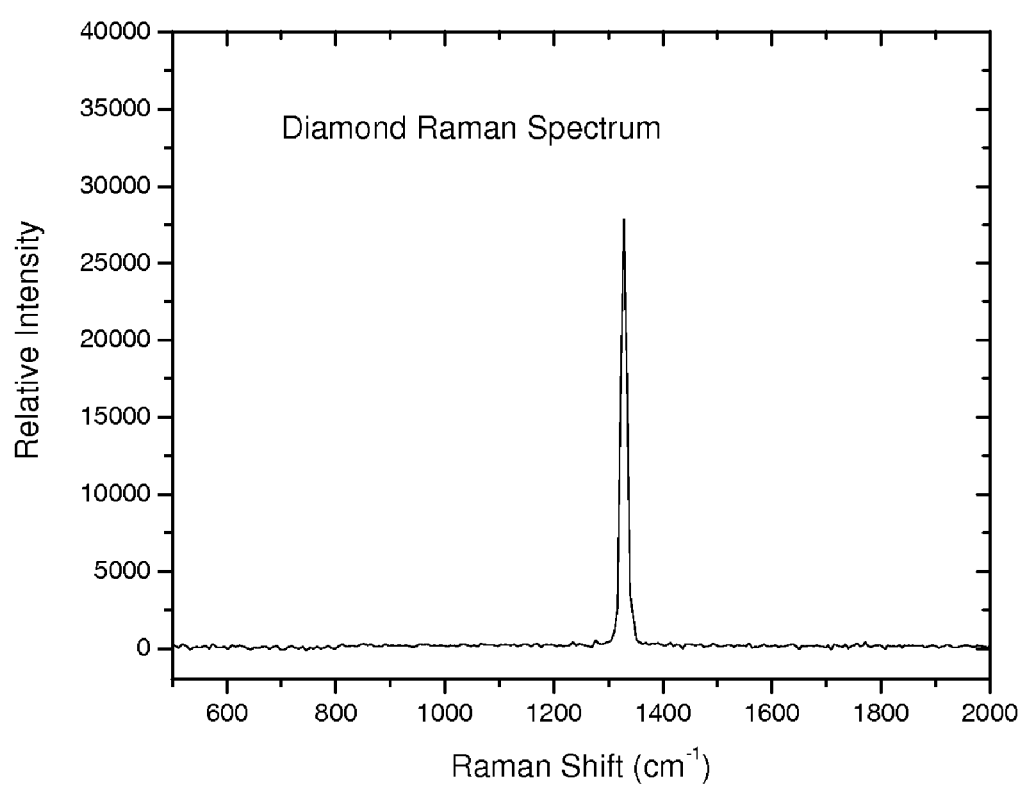
FIG. 3 shows the Raman spectrum of a diamond sample measured by the disclosed Raman spectroscopic apparatus.

FIG. 3 shows the Raman spectrum of a diamond sample measured by the disclosed Raman spectroscopic apparatus. A narrowband Raman scattering signal corresponding to the diamond band at 1332 cm$^{-1}$ can be clearly observed in the obtained spectrum, verifying the capability of the internal grating stabilized broad stripe diode laser for high resolution Raman spectroscopy.

Figure 4:
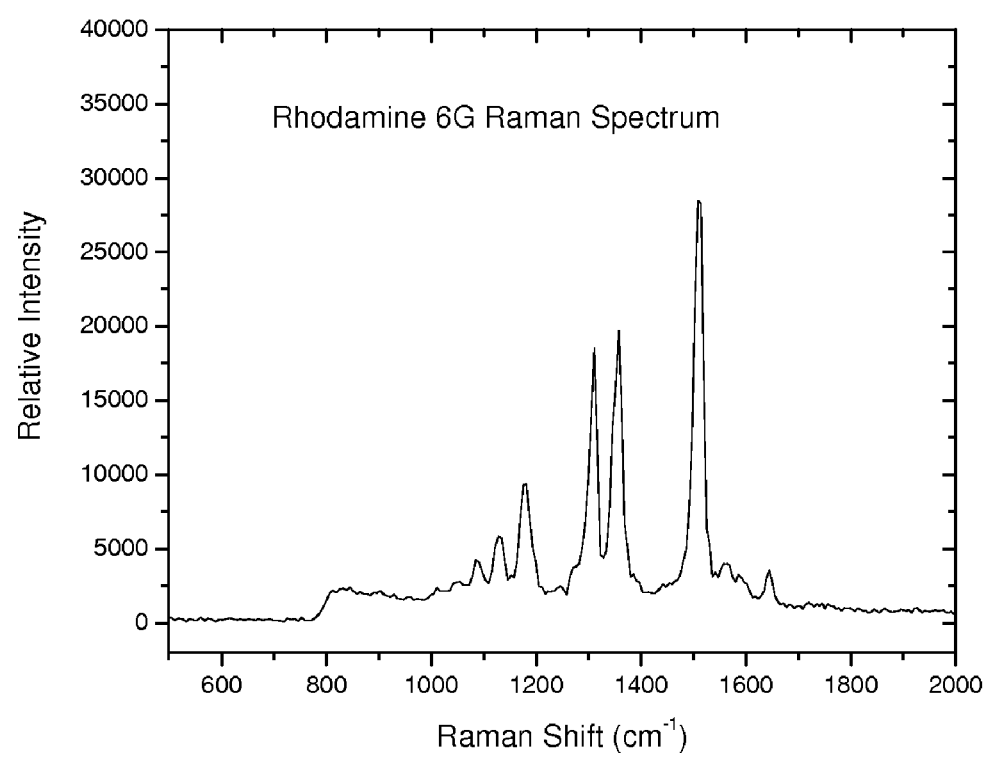
FIG. 4 shows the Raman spectrum of a Rhodamine 6G sample measured by the disclosed Raman spectroscopic apparatus.

FIG. 4 shows the measured Raman spectrum of a Rhodamine 6G sample. The sample is highly fluorescent under visible laser excitation, making it impossible to extract Raman scattering signal from the overwhelming fluorescence background. While with the 988 nm laser excitation, the fluorescence background is completely suppressed and a high resolution Raman spectrum of the sample is revealed.

Figure 5:
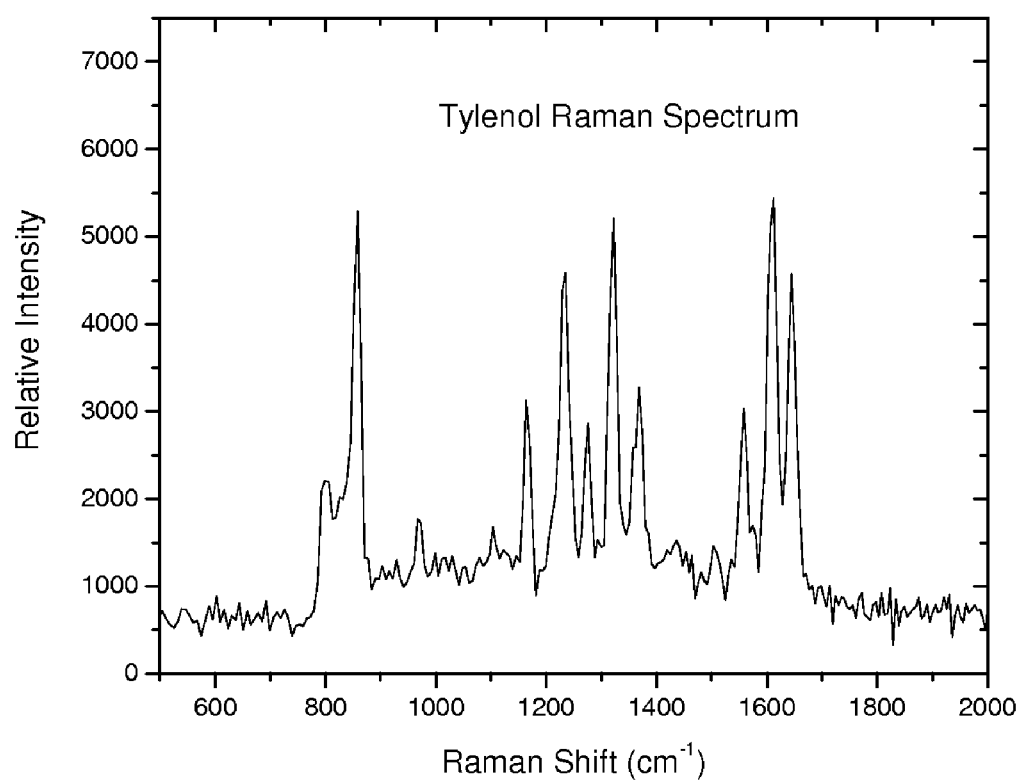
FIG. 5 shows the Raman spectrum of a Tylenol sample measured by the disclosed Raman spectroscopic apparatus.

FIG. 5 shows the measured Raman spectrum of a Tylenol sample. Although the InGaAs array detector has a relatively low responsivity, the high spectral brightness of the laser and the high throughput of the optical probe enable a high quality Raman spectrum to be obtained from the sample.

Referring to FIG. 6, a method for measuring the Raman spectrum of a physical material is provided. The method comprising the steps of: providing a broad stripe diode laser with an internal grating for producing a laser beam with high spectral brightness (Step 602); providing an optical system for delivering said laser beam to a physical material to excite a scattered optical signal, and for extracting a Raman scattering signal from the scattered optical signal, said optical system utilizes the high spectral brightness of the laser for efficient Raman scattering excitation and extraction (Step 604); and providing a spectrograph for measuring the relative intensity of different wavelength components of the Raman scattering signal to obtain a Raman spectrum (Step 604).

It is worth to note that the laser wavelength cited in this exemplary embodiment is for demonstration purposes only. The internal grating technology can be applied to any broad stripe diode lasers with emission wavelength ranging from ultraviolet (UV) to near infrared (NIR). Correspondingly, the Raman spectroscopic apparatus built on the laser can operate in ultraviolet, visible, and infrared wavelength regimes.

In another embodiment of the current invention, the internal grating stabilized laser is utilized to implement a shifted wavelength excitation technique for fluorescence suppression in Raman spectroscopy. The shifted wavelength excitation technique had been proposed by Shreve et al. in Applied Spectroscopy, Vol. 46, No. 4, 1992, p. 707. However, the lack of a low-cost tunable laser light source limits the application of the technique. In this embodiment, two or more internal grating stabilized lasers are employed to provide a laser array with slightly shifted central wavelengths, where laser wavelength control is fulfilled by controlling the Bragg wavelength of the internal grating with an accuracy of <±0.1 nm. By exciting the Raman/fluorescence signal at two or more closely spaced wavelengths and performing a subtraction of the obtained Raman/fluorescence spectra, the fluorescence background, which is not influenced by laser wavelength shift, will be suppressed thereby the weak Raman scattering signal can be extracted from a strong fluorescence background.

Referring to FIG. 7, a method is provided for measuring the Raman spectrum of a physical material that exhibits fluorescence. The method comprises the steps of: providing a plurality of broad stripe diode lasers with internal gratings (Step 702). Each of the lasers has slightly shifted laser wavelengths than others with the difference determined by slightly shifted Bragg wavelengths of the internal gratings. The method further comprises the steps of obtaining a plurality of Raman/fluorescence spectra from the physical material by using the plurality of broad stripe diode lasers as the excitation light source (Step 704); and mathematically manipulating the plurality of Raman/fluorescence spectra to extract a Raman spectrum from the plurality of Raman/fluorescence spectra (Step 706).

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A spectroscopic apparatus for measuring the Raman spectrum of a physical material, the apparatus comprising:
   a broad stripe diode laser with a monolithically integrated narrowband internal grating for producing a laser beam with high spectral and spatial brightness;
   an optical system for delivering said laser beam to a physical material to excite a scattered optical signal, and for extracting a Raman scattering signal from the scattered optical signal, said optical system maintains the spatial brightness of said laser beam; and
   a spectrograph for measuring the relative intensity of different wavelength components of the Raman scattering signal to obtain a Raman spectrum;
   wherein the internal grating acts as a distributed Bragg reflector (DBR) to lock the laser wavelength to a Bragg wavelength set by a period associated with said internal grating and to narrow down a spectral linewidth of the laser.

2. The Raman spectroscopic apparatus of claim 1, wherein the diode laser has an emission wavelength ranging from that of ultraviolet to infrared.

3. A method for measuring the Raman spectrum of a physical material, the method comprising the steps of:
   providing a broad stripe diode laser with a monolithically integrated narrowband internal grating for producing a laser beam with high spectral and spatial brightness;
   providing an optical system for delivering said laser beam to a physical material to excite a scattered optical signal, and for extracting a Raman scattering signal from the scattered optical signal, said optical system maintains the spatial brightness of said laser beam; and
   providing a spectrograph for measuring the relative intensity of different wavelength components of the Raman scattering signal to obtain a Raman spectrum;
   wherein the internal grating acts as a distributed Bragg reflector (DBR) to lock the laser wavelength to a Bragg wavelength set by a period associated with said internal grating and to narrow down a spectral linewidth of the laser.

4. The method of claim 3, wherein the internal grating acts as a distributed Bragg reflector (DBR) to lock the laser wavelength to a Bragg wavelength set by a period associated with said internal grating and narrowing down the spectral linewidth of the laser.

5. The method of claim 3, wherein the diode laser has an emission wavelength ranging from that of ultraviolet to infrared.

6. A method for measuring the Raman spectrum of a physical material that exhibits fluorescence, the method comprising the steps of:

providing a plurality of broad stripe diode lasers with internal gratings, said lasers each having slightly shifted laser wavelengths than other lasers among said plurality of broad stripe diode lasers, with the slightly shifted laser wavelengths being determined by slightly shifted Bragg wavelengths of said internal gratings;

obtaining a plurality of Raman/fluorescence spectra from said physical material by using said plurality of broad stripe diode lasers as the excitation light source; and mathematically manipulating said plurality of Raman/fluorescence spectra to extract a Raman spectrum from said plurality of Raman/fluorescence spectra.

7. The method of claim 6, wherein the internal gratings act as a distributed Bragg reflector (DBR) to lock the laser wavelength to a Bragg wavelength set by a period associated with said internal grating and narrowing down the spectral linewidth of the lasers.

8. The method of claim 6, wherein each of the plurality of broad stripe diode lasers has an emission wavelength ranging from that of ultraviolet to infrared.

9. The method of claim 6, wherein the internal grating is monolithically integrated within the diode laser.

* * * * *